United States Patent [19]

Judd et al.

[11] Patent Number: 4,981,782
[45] Date of Patent: Jan. 1, 1991

[54] SYNTHETIC PEPTIDES FOR DIAGNOSIS AND PREVENTION OF INFLUENZA VIRUS INFECTION AND THEIR USE

[75] Inventors: Amrit K. Judd, Belmont, Calif.; Doris J. Bucher, New York; Steven W. Popple, Brooklyn, both of N.Y.

[73] Assignee: SRI International, Menlo Park, Calif.

[21] Appl. No.: 50,633

[22] Filed: May 14, 1987

[51] Int. Cl.$^5$ ............... C12Q 1/70; G01N 33/536; G01N 33/531; C07K 7/08

[52] U.S. Cl. ............... 435/5; 436/501; 436/536; 436/543; 436/544; 436/545; 436/546; 436/547; 530/300; 530/326; 530/327; 530/335; 530/387; 530/402; 530/810; 530/826; 435/188

[58] Field of Search ............... 435/5, 188; 424/86, 424/89; 436/547, 536, 501, 543; 530/326, 327, 333, 335, 826, 387, 300

[56] References Cited

U.S. PATENT DOCUMENTS

| | | | |
|---|---|---|---|
| 4,588,580 | 5/1986 | Bucher et al. | 435/5 |
| 4,588,680 | 5/1986 | Bucher et al. | 435/5 |
| 4,597,967 | 7/1986 | Beachey | 424/88 |
| 4,625,015 | 11/1986 | Green et al. | 424/86 |
| 4,713,366 | 12/1987 | Stevens | 514/13 |

FOREIGN PATENT DOCUMENTS 8403564  9/1984  PCT Int'l Appl. ............... 435/5

OTHER PUBLICATIONS

Sigma Chemical Co., P.O. Box 14508, St. Louis, Mo. (Feb. 1982).
Gotch et al., *Nature*, vol. 326, pp. 881–882 (Apr. 30, 1987).
Handbook of Experimental Immunology, Weir, D. M. (ed.), vols. 1 and 3, pp. 15.1, 14.1–5 & 18–37 (vol. 1) & pp. 40.2–3, A3.10–17 (vol. 3), Oxford, England, 1978.
Webster et al., (1977) Infection and Immunity 17(3): 561–566.
Kahn et al., (1982) J. Clinical Microbiology 16(5):813–820.
Van Wyke et al., (1984) J. Virol. 49(1):248–252.
McQuillin et al., (1985) Lancet 2:911–914.
Ye et al., (1987), J. Virol. 61(2):239–246.
Joassin et al., (1987) Arch. Virol. 95:183–195.
Bucher et al., (1987) J. Immunol. Methods 96:77–85.
Oxford et al., (1977) Chemical Abstracts 86(3):296, abstract 15052t.
McQuillin et al., (1985) Lancet, vol. II, No. 8461, pp. 911–914.
Petrov et al., (1986) Chemical Abstracts 104(17):510, Abstract 146749p.
Van Wyke et al., (1984) Chemical Abstracts 101:(13):476, Abstract 108664n.
Muller et al., (1982) Proc. Natl. Acad. Sci. 79:(2):569–573.
Donofrio et al., (1986) Chemical Abstracts 105:(5):548, Abstract 40638g.

*Primary Examiner*—Esther L. Kepplinger
*Assistant Examiner*—Janelle Graeter
*Attorney, Agent, or Firm*—Irell & Manella

[57] ABSTRACT

Synthetic polypeptides having influenza virus antigenic properties are disclosed. These polypeptides correspond substantially to particular regions in the matrix protein of influenza virus. Salts, derivatives, and conjugates of these polypeptides are disclosed as well as methods for using these materials for diagnostic and medical/veterinary purposes.

23 Claims, No Drawings

SYNTHETIC PEPTIDES FOR DIAGNOSIS AND PREVENTION OF INFLUENZA VIRUS INFECTION AND THEIR USE

The invention described herein was made in the course of work under a contract from the United States Department of Defense (DAMD)-17-85-C-5 019 United States Army).

BACKGROUND OF THE INVENTION

1. Field of the Invention

The present invention relates to antigens for influenza. More particularly, it relates to synthetic peptide sequences which present influenza antigenic determinants, the use of these sequences as antigens in the preparation of diagnostic reagents and vaccines, the formation of antibodies, and the like and the use of these peptides, reagents, antibodies and vaccines in the diagnosis and prevention of influenza virus infections.

2. Background Materials

The Importance of Influenza

Influenza remains an important infection which can cause epidemics or pandemics following emergence of new strains. A network of surveillance laboratories has been set up worldwide, but despite these efforts influenza is still considerably under-reported. This is at least in part due to the lack of rapid and reliable tests for use in laboratories that are only moderately well equipped. In addition, effective drugs such as amantadine are underused for treatment or prophylaxis, particularly in the elderly, because rapid methods of diagnosis are not commonly available.

The problem is further complicated by the tendency of the responsible virus to continually reappear as different strains. It has been shown that as these new strains emerge they present "drift" or "shift" of their surface antigenic determinants that can make their immunologic identification problematic when based on these determinants. It has been shown that the structure of the matrix protein of the influenza virus is highly conserved from strain to strain.

The Matrix Protein

The matrix protein (or "M protein") of influenza is the major internal protein of the influenza virion. It is known to comprise as much as 46% of the total viral protein, to have a molecular weight of about 27,000 and to line the inner surface of the lipid bilayer of the envelope that contains the virus' hemagglutinin and neuraminidase subunits. Its peptide chain contains 252 amino acids. Its amino acid sequence has been reported.

A number of workers have examined various aspects of matrix protein's role in connection with influenza. Webster and Hinshaw in *Infection and Immunity* (Sept. 1977) 17, (3):561–566 reported that intact isolated M protein enhanced virus clearance in mice. Coinventor Bucher and her coworkers, in *J. Clin. Microbiol.* (Nov. 1982) 16,(5):813–820 used intact isolated M protein in an enzyme-linked immunosorbent assay (ELISA) to detect antibodies to influenza virus.

Other references relating to the properties of the M protein include the report of coinventor Bucher and her coworkers which showed that purified intact M protein can elicit an antibody response in rabbits at a titer of 1:40,000 (*J. Immunol. Methods* (1987) 96:77–85); the report of Van Wyke et al in *J. Virol.* (1984) 49:248–252 of multiple antigenic domains in the M protein structure; and McQuillin et al's work, reported in Lancet (Oct. 26, 1985) 2 (8461); 911–914, on monoclonal antibodies to influenza M protein and their use in influenza diagnosis.

Other Work

Other work related to the general subject of influenza and its diagnosis and treatment includes Grandien, et al, who reported in *J. Clin. Microbiol.* (Nov. 1985) 22(5):757–760 their studies comparing two immunoassay techniques for diagnosis of influenza infections; and Shalit, et al, who reported in *J. Clin. Microbiol.* (Nov. 1985) 22, (5):877–879 their studies comparing monoclonal antibodies and polyclonal antisera for diagnosis of influenza infections.

Other references relating to the general subject of diagnosis of influenza infection include, for example, Julkumen, I, et al, *J. Virol. Methods* (Aug. 1984) 9(1):7–14; Zhurov, S. A., et al, *Za. Microbiol. Epidemiol. Immunobiol.* (Jan. 1985) (1):81–5 (Eng. Abstr.); Ptakova, M., et al, *Acta* Virol. (Praha) (Jan 1985) 29(1):19–24; Bukrinskaia, A. G., *Vopro, Viromol.* (Jan.-Feb. 1985) 30(1):16–21 (61 ref.): Anestad, G., *J. Hyg.* (London) (June 1985) 94(3):349–56; Kobiakova T. N., *Microbiol. Epidemiol. Immunobiol.* (Apr. 1985) (4):43–5; Van Voris, L. P., et al, *J. Med. Virol.* (Aug. 1985) 16(4)315–20: and *Vopro. Viromol.* (July—Aug. 1984) 29(4):417–9; Bucher et al, *J. Immunol. Methods* (1987) 96: 77–85.

These prior studies have been valuable to a general understanding of the influenza virus but have pointed up certain shortcomings. In particular, the use of purified materials such as purified M protein has the problem of contamination and batch-to-batch variation. Monoclonal antibodies, while theoretically attractive, can be of low avidity and low binding constant and thus of low value.

STATEMENT OF THE INVENTION

It has now been found that certain synthetic polypeptides can react with preformed antibody to influenza A M protein, can stimulate influenza A M protein antibody response and can potentially serve as replacements for the native M protein in the selective diagnosis of infection with a wide range of strains of influenza virus. This antigenic reactivity of these proteins offers the potential that they can also be used as vaccinating agents to generate antibodies useful for prevention and/or treatment of a wide range of influenza A infections.

In particular, it has been found according to the present invention that synthetic polypeptides having from 15 to 25 amino acid residues substantially corresponding to 15 to 25 amino acid sequences in the 79 through 104 region of type A influenza M protein, have high influenza antigenic reactivity.

Similarly, it has been found according to the present invention that synthetic polypeptides having from 9 to 15 amino acid residues substantially corresponding to 9 to 15 amino acid sequences in the 64 through 80 region of type A influenza M protein, have high influenza antigenic reactivity.

In addition, it has been found according to the present invention that synthetic polypeptides having from 12 to 21 amino acid residues substantially corresponding to 12 to 21 amino acid sequences in the 149 through 169 region of type A influenza M protein, also have high influenza antigenic reactivity.

In other aspects, the invention concerns the salts of these polypeptides, the amide and acyl derivatives of the carbonyl and amino end groups of these polypeptides and their salts, and conjugates of these polypeptides with macromolecular carriers.

In an additional aspect, the invention concerns labelled versions of these polypeptides, their corresponding salts, derivatives and conjugates and their application to label-dependent assay methods such as radioimmunoassays (RIA) and enzyme-linked immunosorbent assays (ELISA).

In another aspect, this invention concerns methods of detecting the presence of influenza virus or diagnosing a state of influenza infection in an avian species or a mammalian species, particularly a human being, which methods are based on these synthetic polypeptides. In one of these methods, a sample taken from the subject is contacted under immunologic reaction conditions with a peptide of this invention, its salt, or its conjugate optionally suitably labeled. If the subject was infected with influenza, the subject's sample will also contain antibodies to the influenza virus. The present peptides (or salts or conjugates) will react immunologically with a broad range of such antibodies. The occurrence or nonoccurrence of this immunologic reaction can be followed with conventional reporter mechanisms such as the ELISA or EMIT methods. radiolabels, fluorolabels or the like.

In a second representative example of these methods, the peptide or its salt or conjugate, optionally suitably labeled, competes with antigen in the sample for a quantity of added antibody with the results being based on the relative reaction of the competing antigen and peptide.

In another aspect, this invention relates to antibodies to these synthetic peptides or their salts or conjugates. These antibodies may be developed using a polypeptide (or a pharmaceutically acceptable salt thereof, or a conjugate of the peptide or a pharmaceutically acceptable salt thereof) as an immunogen to develop antibodies in a suitable host animal. Such antibodies may be used as diagnostic reagents in antibody-based assays such as the ELISA or EMIT assays or radioimmunoassay (RIA) techniques. The pure synthetic polypeptides, conjugates thereof, or antibodies prepared following this technique may also serve as calibration reagents in the ELISA, or EMIT, techniques as well as in other immunological assay techniques.

In another aspect, this invention concerns a method for immunization against influenza in a mammalian or avian species, particularly a human being, wherein the method comprises administering to the subject in need of such treatment a therapeutically effective amount of one or more or the synthetic polypeptides of the invention or a pharmaceutically acceptable salt or conjugate thereof or a vaccine produced therefrom, optionally in a pharmaceutically suitable adjuvant, carrier or diluent.

As yet another aspect, this invention also concerns the use of the antibodies against the synthetic polypeptides or their conjugates or salts in methods of treatment of influenza. In such processes, the antibodies may serve as therapeutic agents by "passive immunization", a technique wherein partially purified immune sera from host animals or from hybridoma cell lines is to be injected into the influenza patient and has a therapeutic effect by binding to and neutralizing the infecting influenza virus.

DETAILED DESCRIPTION OF THE INVENTION

Definitions

In the specification and claims, reference will be made to certain terms which are defined as follows.

As used herein:

"Acyl" refers to an alkyl-containing carbonyl group, e.g.. R—C(=O)—, wherein R is an alkyl group having from 1 to 8 carbon atoms, such as methyl, ethyl, n-propyl, isopropyl, hexyl, octyl and the like. The acyl group usually preferred in this invention is acetyl. Acyl groups are used to block the terminal amino group of a polypeptide.

"Antibody" refers to a member of a family of glycosylated proteins called immunoglobulins, which can specifically combine with an antigen such as influenza antigen.

"Antigen" refers to a protein or peptide compound which will give rise to antibody formation.

"Antigenic determinant" or "antigenic determinant site" refers to the actual site of antibody recognition of the antigen. The term is used interchangeably with "epitope".

"Carrier" refers to a high molecular weight (macromolecular) polymeric material, usually a protein, to which an antigen or hapten can be bound or conjugated so as to facilitate antibody formation. Carriers can incorporate labels in their structure, if desired.

"Conjugate" refers to an antigen or hapten chemically bonded to a carrier; a conjugate can contain other groups, as well.

"ELISA" refers to an enzyme-linked immunosorbent assay which employs an antibody or antigen bound to a solid phase and an enzyme-antigen or enzyme-antibody conjugate to detect and quantify the amount of antigen or antibody present in a sample. A description of the ELISA technique is found in Chapter 22 of the 4th Edition of *Basic and Clinical Immunology* by D. P. Sites et al. published by Lange Medical publications of Los Altos, Calif., in 1982, which is incorporated herein by reference.

"EMIT" refers to an enzyme-multiplied immunoassay technique which uses (1) an enzyme-labeled hapten, (2) specific antibody to the hapten, (3) pretreatment reagent, (4) huffered-enzyme substrate, and (5) standards to detect the amount of an unknown in a sample. A description of the EMIT technique is found in *Enzyme Immunoassay*, edited by E. T. Maggio, published in 1980 by CRC press, Inc., Boca Raton, Fla., particularly on pp. 141–150, 234–5, and 242–3. These materials are incorporated by reference.

"Epitope" refers to that portion of a molecule which is specifically recognized by an antibody. It is also referred to as a determinant.

"Fluoroimmunoassay" refers to an antibody-based assay in which the species to be measured binds to, displaces or competes for binding with a material labelled with a fluorescent species in an antibody-ligand complex. In some embodiments of this assay, the complex is separated and the presence or absence of fluorescent species gives a measure of the amount of measured species. In other embodiments, the complex has different fluorescent properties than the uncomplexed fluorescent species so that the formation of the complex can be detected without separation of the complex. A description of fluoroimmunoassay techniques is found in "A Review of Fluoroimmunoassay and Immunofluorometric Assay", D. S. Smith et al, *Ann Clin. Biochem* (1981) 18:253-274 which is incorporated herein by reference.

"Hapten" refers to a compound, usually of low molecular weight, which when bound to a larger molecule can give rise to antibody formation.

"Influenza" refers to a disease state brought about by infection by an influenza virus. Among the influenza viruses are Type A and Type B viruses. These Type A and B are recognized in the field. A number of these have been identified and are present in and available from the American Type Culture Collection. These representative materials are described at pages 272-276 in "American Type Culture Collection Catalogue of Strains II, Fourth Edition" (1983), R. Hay, et al, Eds, American Type Culture Collection, Rockville, Md. which is incorporated herein by reference.

"Label" refers to a detectable group in a molecule. Among the common labels are radioactive species useful in radioimmunoassays, fluorescent species useful in fluoroimmunoassays, and enzymatic species useful in the ELISA and EMIT methods and the like.

"Ligand" refers to any molecule which has an antibody combining site and can bind to a receptor.

"Lower alkyl" refers to a straight or branched chain saturated hydrocarbon group having from 1 to 4 carbon atoms such as, for example, methyl, ethyl, n-propyl, isopropyl, n-butyl, isobutyl, sec-butyl, and tert-butyl.

"Matrix protein" or "M protein" refer to a protein constituent of influenza and related viruses. It is described in detail herein in the Background section.

"peptide" or "polypeptide" refers to relatively low molecular weight compounds which yield two or more amino acids on hydrolysis.

"pharmaceutically acceptable salt" and "salt" refer to salts that retain the desired antigenic activity of the parent polypeptide. "pharmaceutically acceptable salt" refers to salts that are suitable for ingestion or parenteral administration or the like in that they do not impart any undesired toxicological effects. Examples of such salts and pharmaceutically acceptable salts include (a) acid addition salts formed with inorganic acids for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid benzoic acid, tannic acid, alginic acid, polyglutamic acid, naphthalenesulfonic acids, naphthalenedisulfonic acids, polygalacturonic acid, and the like; (b) salts with monovalent and polyvalent metal cations such as sodium, potassium zinc calcium, barium, magnesium, aluminum, copper, cobalt, nickel, cadmium, and the like; or with an organic cation formed from N,N'-dibenzylethylenediamine or ethylenediamine; and (c) combinations of (a) and (b), e.g., a zinc tannate salt and the like.

"Radioimmunoassay" or "RIA" refers to an antibody-based assay in which the species to be measured binds to, displaces or competes for binding with a radiolabeled material in an antibody-ligand complex. The complex is separated and the presence or absence of radioactivity gives a measure of the amount of measured species.

"Receptor" refers to a region of an antibody With the capability to combine specifically with an antigen.

"Substantially corresponding" refers to the property of two amino acid sequences being identical to one another or differing from one another by no more than two amino acid units. Sequences can differ by having a different amino acid at a given position or by having an extra amino acid or by missing an amino acid, preferably, the sequences have at most one point of difference and more preferably are identical.

"Vaccine" refers to a suspension or solution of attenuated or killed microorganisms (specifically, influenza virus) or synthetic polypeptides or conjugates administered for the prevention, amelioration or treatment of influenza via stimulation of the production of specific antibodies against the influenza virus.

As used herein, the following abbreviations are used for the amino acids described:

| | |
|---|---|
| Alanine | Ala |
| Arginine | Arg |
| Asparagine | Asn |
| Aspartic Acid | Asp |
| Cysteine | Cys |
| Glutamine | Gln |
| Glutamic Acid | Glu |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |

These represent L-amino acids with the exception of the achiral amino acid glycine. All peptide sequences mentioned herein are written according to the generally accepted convention whereby the N-terminal (or amino-terminal) amino acid is on the left and C-terminal (carboxyl-terminal) amino acid is on the right.

DESCRIPTION OF PREFERRED EMBODIMENTS

In one aspect, this invention relates to synthetic peptide sequences which have influenza antigen properties.

One such synthetic sequence has about 15 to 25 amino acids substantially corresponding to a 15 to 25 amino acid sequence of the 79-104 region of the type A influenza virus matrix protein. The 79-104 region of the matrix protein has the sequence $$\text{H—Phe—Val—Gln—Asn—Ala—Leu—Asn—Gly—Asn—Gly—Asp—Pro—Asn—Asn—Met—Asp—Lys—Ala—Val—Lys—Leu—Tyr—Arg—Lys—Leu—Lys—OH}$$

(positions 80, 90, 100 indicated)

In preferred embodiments, the synthetic sequence is from to 20 amino acids in length and substantially corresponds to the 80–103 region. More preferably, it is 18 amino acids in length and substantially corresponds to the 83–100 region. An especially preferred embodiment has the amino acid sequence:

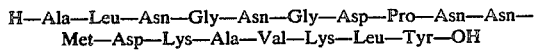
A second such synthetic sequence has about 9 to 15 amino acids substantially corresponding to a 9 to 15 amino acid sequence of the 64–80 region of the type A influenza virus mat nitro, p-toluenesulfonyl, 4-methoxybenzenesulfonyl, Z, Boc, and adamantyloxy carbonyl; for tyrosine: benzyl, o-bromobenzyloxycarbonyl, 2,6-dichlorobenzyl, isopropyl, cyclohexyl, cyclopentyl, and acetyl; for serine: benzyl and tetrahydropyranyl; for histidine: benzyl, p-toluenesulfonyl and 2,4-dinitrophenyl.

The carboxyl-terminal amino acid is attached to a suitable solid support. Suitable supports are inert to the reagents and reaction conditions of the reactions, as well as insoluble in the media used. Suitable supports include chloromethylpolystyrenedivinylbenzene polymers and the like, especially chloromethylpolystyrene-1% divinylbenzene polymer. For the special case where the carboxy-terminal amino acid of the peptide becomes an amide [—C(=O)—NH$_2$], a particularly useful support is the benzhydrylamino-polystyrene-divinylbenzene polymer described by p. Vivaille et al, Helv Chim Acta (1971) 54:2772. The attachment to the chloro-methyl polystyrene-divinylbenzene type of resin is made by means of the reaction of the N$^\alpha$-protected amino acid, especially the Boc-amino acid, as its cesium, tetramethylammonium, 4,5-diazabicyclo[5.4.0]undec-5-ene, or similar salt in ethanol, acetonitrile, N,N-dimethylformamide (DMF), and the like, especially the cesium salt in DMF, with the chloromethyl resins at an elevated temperature, for example between about 40° and 60° C., preferably about 50° C., for from about 12 to 48 hours, preferably about 24 hours. The N$^\alpha$-Boc-amino acid is attached to the benzhydrylamine resin by means of an N,N'-dicyclohexylcarbodiimide (DCC)/1-hydroxybenzotriazole (HBT) mediated coupling for from about 2 to about 24 hours, preferably about 12 hours at a temperature of between about 10° and 50° C., preferably 25° C. in a solvent such as dichloromethane or DMF, preferably dichloromethane.

The removal of the N$^\alpha$-protecting groups may be performed in the presence of, for example, a solution of trifluoroacetic acid in methylene chloride, or other strong acid solution, preferably 50% trifluoroacetic acid in dichloromethane at about ambient temperature. Base-labile protecting groups may be removed by treatment with a base such as piperidine in DMF. Each protected amino acid is preferably introduced in approximately 2.5 molar excess and coupling may be carried out in dichloromethane and the like, especially in methylene chloride at about ambient temperature. The coupling agent is normally DCC in dichloromethane but may be N,N'-diisopropylcarbodiimide or other carbodiimide either alone or in the presence of HBT, N-hydroxysuccinimide, other N-hydroxyimides or oximes. Alternatively, protected amino acid active esters (e.g., p-nitrophenyl, pentafluorophenyl and the like) or symmetrical anhydrides may be used.

At the end of the solid phase synthesis, the polypeptide is either carried through another deprotection and neutralization cycle followed by acylation, preferably acetylation with acetic anhydride to yield an N-acetyl (N-Ac) blocked amino end group, or it may be removed from the resin directly. If the carboxy [—C(=O)—OH] terminal is to be blocked as the amide, the peptide may be either synthesized on the benzhydrylamino-polystyrene resin, which gives the amide directly, or it may be removed from the resin by ammonolysis with, for example, ammonia/methanol or ammonia/ethanol, at a temperature of from about 0° to about 50° C. preferably about 25° C. for about 12 to about 48 hours, preferably about 18 hours. If a peptide with a free amino-terminal and a carboxyl-terminal is desired, the peptide may be directly removed from the resin by treatment with anhydrous liquid hydrogen fluoride in the presence of a radical scavenger such as anisole. The amino- or carboxyl-blocked (protected) peptides, either on the resin or removed from the resin by ammonolysis, are similarly deprotected by treatment with anhydrous liquid hydrogen fluoride. In cases where base-labile protection of the N$^\alpha$ function is used in conjunction with t-butyl-based side chain protection, the final resin removal and deprotection step may be performed with trifluoroacetic acid.

Other means of removal of the (side chain) protecting groups from the polypeptide are treatment with hydrogen fluoride/pyridine complex, treatment with tris(trifluoroacetyl)boron and trifluoroacetic acid, by reduction with hydrogen and palladium on carbon or polyvinylpyrrolidone, or by reduction with sodium in liquid ammonia or with liquid hydrogen fluoride plus anisole at a temperature between about $-10°$ and $+10°$ C., preferably about 0° C., for between about 15 minutes and 1 hour, preferably about 30 minutes. The latter treatment (HF/anisole) may be used for simultaneous cleavage from the resin and deprotection to yield free-CO$_2$H end groups when a normal benzylester linkage has been used or to form a CO—NH$_2$ (amide) end groups when a benzhydrylamino linkage has been used. For the amide terminal peptides on the benzhydrylamine resins, the resin cleavage and deprotection steps may be combined in a single step utilizing liquid HF/anisole as described above. The fully protected polypeptide can then be purified by chromatographic steps.

Salt Formation

The peptides can be obtained as salts, by simple adjustment of the pH of the medium from which they are finally recovered with acids or bases corresponding to the desired counter ions.

Conjugation to Carriers

The polypeptides described herein can be coupled to carriers through several types of functional groups on the polypeptides. These include (a) $\alpha$ or $\epsilon$-amino groups, (b) $\alpha$, $\beta$, or $\gamma$-carboxyl groups. (c) thiol groups, and (d) aromatic rings in the peptides.

$\alpha$ and $\gamma$-amino groups can be coupled by several methods. In one they are reacted with activated carboxyl groups in the carrier. This activation can be carried out with carbodiimides, especially water soluble carbodiimides (WSC) such as N-ethyl-N'-(3-dimethylaminopropylcarbodiimide). isoxazolium salts, 1-ethoxycarbonyl-2-ethoxyl, 2-dihydroquinoline, active ester forming reagents (to yield N-hydroxysuccinimide esters, 1-hydroxybenzotriazole esters, nitrophenyl esters, pentafluorophenyl esters, etc.), reagents yielding acid chlorides (e.g., PCl$_5$, but only for nonprotein carriers), reagents yielding mixed anhydrides (e.g.,acetic anhydride) and the like.

The free amino function of the synthetic peptide (either the $\alpha$-amino function or an $\epsilon$-amino function of lysine) is then reacted with the activated carboxyl function of the carrier in an aqueous buffer or in a mixed organic/aqueous buffer system (e.g., DMF/water), pH 8). For nonprotein carriers, an organic solvent (e.g., DMF) may be used. Especially useful techniques in this class are concurrent activation of a protein carrier with and coupling with peptide in aqueous buffer or preparation of the p-NO$_2$-phenyl ester of a succinylated protein carrier followed by coupling with the peptides in aqueous buffer.

In another method, the amino function(s) on the synthetic peptide may be cross-linked with amino functions on the carrier molecule by reaction with glutaraldehyde in aqueous solution on mixed organic/aqueous solution (pH ~7) at room temperature, or by reaction with bifunctional cross-linking reagents such as dimethylsuberimidate, phenyldiisocyanate, phenyldiisothiocyanate, difluorodinitrobenzene, or cyanic chloride.

$\alpha$, $\beta$, or $\gamma$-carboxyl groups on the peptides can be reacted with amines on the carrier in the converse of the above process The carboxyl functions on the synthetic peptide will be activated by the techniques just recited. The activated carboxyl functions will then be reacted with the amino functions on a suitable carrier molecule using the aqueous or mixed organic/aqueous buffer conditions described above.

Thiol (—SH) groups present on the synthetic polypeptide chain can be reacted with carriers which have been modified by the incorporation of maleimide functions. The —SH function inserts specifically into the double bond of the maleimide function and yields a peptide-carrier complex. The SH function may be incorporated into the peptide by reaction of an amino function ($\alpha$-amino or $\epsilon$-amino of lysine) with cysteine thiolacetone.

Aromaric rings present in the peptides' Tyr and His units may be cross-linked to the aromatic rings of Tyr and His residues of protein carrier by means of bis-diazotized aromatic compounds (e.g., bis-diazotized benzidine or bis-diazotized o-anisidide). This reaction is performed on an aqueous or mixed organic/aqueous solution of the antigen and carrier. For a review of such techniques, see B. F. Erlanger in *Methods of Enzymology* (1980), 70:85, "The preparation of Antigenic Hapten-Carrier Conjugates—A Survey".

Preparing Labeled Versions of the Peptides

Radiolabeled versions of the polypeptides can be produced in several manners. For one, commercially available $^{14}$carbon-labeled amino acids can be employed in the synthesis of the polypeptides. Similarly $^3$H-amino acids can be prepared by the magnesium oxide procedure of Schwyzer et al, *Helv. Clin. Acta*, 42 2622 (1959). Except for the precautions routinely associated with radiochemicals, these processes can follow the usual synthesis route. Alternatively, the finished polypeptide or conjugate can be radiolabeled by tritium exchange.

Enzyme labels can be incorporated by using an enzymic carrier for forming conjugates or by attaching an enzymatically active group to the carrier or the peptide.

GENERATION OF ANTIBODIES TO THE SYNTHETIC PEPTIDES

Methods for generating antibodies to antigens using host animals are known generally to the art. In a typical preparation, one or more of the synthetic polypeptide sequences is introduced into a mammalian or avian host. Suitable hosts include, for example, monkeys, cattle, rabbits, rats, mice, and the like.

This is usually accomplished by subcutaneous injection as a solution in saline which has been emulsified with complete Freund's adjuvant.

The antibodies are collected by bleeding the animal after about a month. The whole blood is allowed to clot at 25° C. for several hours. Aqueous ammonium sulfate solution is added to achieve 40% by weight of aqueous solution, and the IgG fraction precipitates. The precipitate is collected by centrifugation and resuspended in saline or buffer solution to the desired concentration.

The purified antibody fraction may be further modified for use in diagnostic assay systems. Such modification may encompass linkage with enzymes such as lipozyme, lactoperoxidase, alkaline phosphatase and others for use in ELISA assays. The antibody may be modified with fluorescent moieties. Optimally, this fluorescence may be quenched or enhanced upon binding of the antibody and antigen. These techniques for assaying the extent of the antibody-antigen interaction are known in the art. An essential first step is, however, the preparation of suitably immunogenic synthetic influenza polypeptide for administration to the animals so that a population of high affinity antibodies will be obtained.

UTILITY AND ADMINISTRATION

In the practice of the medical and veterinary methods of this invention an effective amount of a polypeptide or conjugate or antibody thereto of this invention or a pharmaceutical composition containing the same is administered to the subject in need of such treatment. These polypeptides, conjugates or antibodies or compositions may be administered by any of a variety of routes depending upon the specific end use, including particularly parenterally (including subcutaneous, intramuscular, and intravenous administration). Oral administration can also be used, particularly with stable forms of these materials. The most suitable route in any given case will depend upon the use, particular active ingredient, the subject involved, and judgment of the medical or veterinary practitioner.

The materials can be administered to mammals such as man, monkeys, dogs, rodents, and the like, and to nonmammalian species such as avian, for example, domestic fowl, including turkeys, chickens, ducks, and the like.

In such uses, the composites generally include a pharmaceutical diluent such as injectable saline, mineral oil or the like. For oral administration, tablets, including enteric-coated tablets, may be used, and in the case of veterinary applications, oral administration can be effected using treated feeds. The compound or composition may also be administered by means of slow-release, depot, or implant formulations, as is well known in the art. The polypeptides, polypeptide conjugates and antibodies described herein are usually administered in amounts of 1 to 1000 $\mu$g per kg of body weight, particularly in amounts of 5–600 $\mu$g per kg of body weight.

For active immunity, the polypeptide or the polypeptide conjugate is administered to produce influenza antibodies in the subject in need of treatment. In passive immunity, partially purified serum containing antibodies from host animals is introduced into the subject to produce a therapeutic effect.

The polypeptides, polypeptide conjugates and antibodies to these polypeptides and polypeptide conjugates of this invention are also useful in the detection and diagnosis of influenza, particularly in providing high purity materials useful for calibration solutions for assay techniques, such as ELISA or EMIT.

The enzymes for use in the diagnostic reagents, standards or kits can vary widely, depending on the ease of conjugation, turnover rate, and the physiological fluid in which the unknown (analyte) is to be measured. Representative enzymes of choice include hydrolysases, nucleases, amidases, esterases and the like which are found in U.S. Pat. No. 3,817,837, which is incorporated herein by reference.

The methods and apparatus for labeling an antibody as described herein for use in a diagnostic reagent, standard or kit is found in U.S. Pat. No. 4,366,241, which is incorporated herein by reference.

EXAMPLES

The following examples serve to illustrate the invention. The should not be construed as narrowing it, or limiting its scope.

EXAMPLE 1

Preparation of
H-Leu-Thr-Val-Pro-Ser-Glu-Arg-Gly-Leu-Gln-Arg-Arg-Arg-OH

This peptide is synthesized by solid-phase techniques on a Beckman Model 990C peptide synthesizer using commercially available t-Boc amino acid polystyrene resin and t-Boc protected amino acids with the following side-chain protecting groups: 0-benzyl esters for Asp and Glu; 0-benzyl ethers for Thr and Ser; tosyl for Arg; dnp for His; p-methoxybenzyl for Cys; ortho-chlorobenzyloxycarbonyl for Lys; and 2,6-dichlorobenzyl for Tyr. All couplings are performed using a 3-molar excess of t-Boc amino acid and dicyclohexyl carbodiimide (DCC) over the number of milli-equivalents of amino acid on the resin. In the case of Asn and Gln, a 3-molar excess of the t-Boc amino acid, DCC, and N-hydroxybenzotriazole (HOBT) are used. All couplings are monitored by the ninhydrin test (Kaiser, et al. *Anal Biochem* 34:595 (1970).) Forty percent TFA-$CH_2Cl_2$ is used for Boc deprotection. 2-Mercaptoethanol (0.1%) is added to the TFA/$CH_2Cl_2$ when methionine is present. (Methionine is used with an unprotected sulfhydryl side chain.) The details of the synthetic cycle are given in Table 1.

TABLE 1

SCHEDULE OF EVENTS FOR ASSEMBLING THE PEPTIDE ON RESIN

| Step | Reagent or Solvent | | Time(min) |
|---|---|---|---|
| 1 | $CH_2Cl_2$ | 3 times | 1.5 |
| 2 | 40% TFA/$CH_2CL_2$ prewash | | 5 |
| 3 | 40% TFA/$CH_2Cl_2$ | | 30 |
| 4 | $CH_2Cl_2$ | 6 times | 1.5 |
| 5 | 80% Isopropanol/$CH_2Cl_2$ | 3 times | 1.5 |
| 6 | $CH_2Cl_2$ | 3 times | 1.5 |
| 7 | 5% Diisopropylethylamine/$CH_2Cl_2$ | 2 times | 10 |
| 8 | $CH_2Cl_2$ | 3 times | 1.5 |
| 9 | Coupling: 3-fold excess of t-Boc amino acid in $CH_2Cl_2$:DMF (2:1, v/v); DCC/$CH_2Cl_2$ | | 120 |
| 10 | $CH_2Cl_2$ | 3 times | 1.5 |
| 11 | 80% Isopropanol/$CH_2Cl_2$ | 3 times | 1.5 |

After completion cf the synthesis, the peptide is cleaved from the resin using a low-high HF procedure (see Tam et al, *Tett. Lett.* 23, 2939 (1982) and *J. Am. Chem. Soc.*, 105, 6442 (1983)), and $S_N2$ deprotection reaction in HF-reaction Apparatus TYpe II (Peninsula Labs). The peptide resin is first treated with an HF:dimethylsulfide:p-cresol mixture (25:65:10) at 4° C. for 1 hr. HF and dimethyl-sulfide are evaporated completely. Next, more HF is distilled into the reaction vessel to make the ratio of HF-p-cresol 9:1. The mixture stirred at 4° C. for 45 min. After that, HF is evaporated completely, first at 4° C. and then at room temperature, under vacuum. At low HF concentration, Asp and Glu side-chain benzyl ester groups are cleaved, with minimum acylation side reactions. The high-HF step removes more acid-stable groups such as Arg (Tos) and cleaves the peptide from the resin completely. The DNP group of His is removed before HF cleavage by treatment with 1000-fold excess of 2-mercaptoethanol.

The peptide is separated from the various side products by extraction with ether and isolated from the resin by extraction with 5% (or higher, depending on the solubility of the peptide) acetic acid and subsequent lyophilization. The crude peptides is subjected to gel filtration on Sephadex LH-20. Final purification is achieved on HPLC using 50 cm/20 mm preparative column packed with Vydac 15–20 μ $C_{18}$. The purity of the peptide is checked by analytical HPLC and amino acid analysis.

After three lyophilizations from water, pure H-Leu-Thr-Val-Phe-Ser-Glu-Arg-Gly-Leu-Gln-Arg-Arg-Arg-OH is obtained as the acetate salt. In the tests which follow, this "66–78" sequence is referred to as "Peptide 1".

EXAMPLE 2

Preparation of
H-Ala-Leu-Asn-Gly-Asn-Gly-Asp-Pro-Asn-Asn-Met-Asp-Lys-Ala-Val-Lys-Leu-Tyr-OH Repeating the procedure of Example 1, but using appropriately protected and unprotected amino acids, H-Ala-Leu-Asn-Gly-Asn-Gly-Asp-Pro-Asn-Asn-Met-Asp-Lys-Ala-Val-Lys-Leu-Tyr-OH is prepared and recovered. In the tests which follow, this "83–100" sequence is referred to as "Peptide 2".

EXAMPLE 3

Preparation of
H-Glu-Gln-Ile-Ala-Asp-Ser-Gln-His-Arg-Ser-His-Arg-Gln-Met-Val-OH

Repeating the procedure of Example 1, but using appropriately protected and unprotected amino acids, H-Glu-Gln-Ile-Ala-Asp-Ser-Gln-His-Arg-Ser-His-Arg-Gln-Met-Val-OH is prepared and recovered. In the tests which follow, this "150–166" sequence is referred to as "Peptide 3".

EXAMPLE 4

Preparation of Radiolabeled
H-Glu-Gln-Ile-Ala-Asp-Ser-Gln-His-Arg-Ser-His-Arg-Gln-Met-Val-OH The process of example 1 is repeated using a radiolabeled Boc-amino acid prepared by the method of Schwyzer et al, *Helv. Chim. Acta* (1959) 42, 2622. This produces the desired radiolabeled product.

EXAMPLE 5

Preparation of Conjugates

The peptides synthesized in Examples 1, 2, 3 and 4 are conjugated to proteins. Keyhole limpet hemocyanin (KLH) is used as the carrier. Conjugation is carried out using the general procedure outlined herein and the specific techniques reported by Bhalnagar et al, *Proc. Natl. Acad. Sci.* (USA) (1986) 79, 4400, incorporated herein by reference.

Activity Tests

The activity of the products of Examples 1 through 3 was tested. Antisera generated by immunization of experimental animals (rabbits) with several influenza type A viruses are reactive with these peptides in an ELISA system. The results are shown in Tables 2 through 4. Similar results were observed in two other species.

Eighteen out of 20 rabbit sera examined show an increase in antibody level to the synthetic polypeptide of Example 1 following immunization with various type A influenza viruses with a mean-fold increase of 60.8 and a median-fold increase of 8.0 (Table 2).

Nineteen out of 20 rabbit sera examined show an increase in antibody level to the synthetic polypeptide of Example 2 following immunization with various type A influenza viruses with a mean-fold increase of 28.1 and a median-fold increase of 4.2 (Table 3).

Fifteen out of 20 rabbit sera examined show an increase in antibody level to the sYnthetic polypeptide of Example 3 following immunization with various type A influenza viruses with a mean-fold increase of 12.9 and a median-fold increase of 4.3 (Table 4).

These results demonstrate that immunization with influenza viruses from a range of subtypes results in production of antibodies which are reactive with the synthetic peptides.

TABLE 2

Titers of Rabbit Antisera to M-Protein Following Immunization with Various Type A Influenza Viruses

| | M-Protein | | | Peptide #1 | | |
|---|---|---|---|---|---|---|
| | Serum Titers | | Ratio Immune/ | Serum Titers | | Ratio Immune/ |
| Virus | Preimmune | Immune | Preimmune | Preimmune | Immune | Preimmune |
| H1N1[a] | | | | | | |
| A/NWS/33[b] | 178 | 161,889 | 909.5 | 177 | 39,136 | 221.1 |
| A/NWS/33[c] | 104 | 336,634 | 3236.9 | 30 | 16,492 | 549.7 |
| A/PR/8/34 | 810 | 313,096 | 386.5 | 718 | 62,486 | 87.0 |
| A/Swine/Cam/39 | 479 | 168,042 | 350.8 | N.D. | 1,041° | — |
| A/USSR/90/77 | 741 | 158,161 | 213.4 | 1278 | 4,658 | 3.6 |
| A/Brazil/11/78 | 730 | 47,809 | 65.5 | 802 | 2,195 | 2.7 |
| H1N2 | | | | | | |
| X-7[e] | 143 | 50,957 | 356.3 | 41 | 627 | 15.3 |
| X-7(F1)[f] | 226 | 68,592 | 303.5 | 242 | 1,308 | 5.4 |
| PR8/HK[g] #2071 | 188 | 15,405 | 81.9 | 206 | 537 | 2.6 |
| PR8/HK[h] #2072 | 155 | 24,300 | 156.8 | 65 | 2,338 | 36.0 |
| PR8/HK[i] #3642 | 232 | 70,956 | 305.8 | 1013 | 7,223 | 7.1 |
| PR8/HK[j] #3643 | 153 | 23,183 | 151.5 | N.D. | 1,688° | — |
| PR8/HK[k] #3644 | 73 | 35,700 | 489.0 | 36 | 1,759 | 48.9 |
| H2N2 | | | | | | |
| A/RI/5$^{-}$/57 | 142 | 20,889 | 147.1 | 117 | 2,161 | 18.5 |
| H3N2 | | | | | | |
| A/Victoria/3/75 | 749 | 35,182 | 47.0 | 725 | 5,718 | 7.9 |
| A/Texas/1/77 | 1010 | 2,046 | 2.0 | 712 | 225 | 0.3 |
| X-31[l] | 699 | 49,851 | 71.3 | N.D. | 772° | — |
| X-73[m] | 590 | 49,239 | 83.5 | 361 | 6,916 | 19.2 |
| X-79[n] | 2403 | 43,011 | 17.9 | 6,640 | 2,257 | 0.3 |
| H7N2 | | | | | | |
| X-74[o] | 207 | 18,528 | 89.5 | 82 | 672 | 8.2 |
| Mean | 501 | 84,674 | 373.3 | 779 | 9,218 | 60.8 |
| Median | 229 | 48,524 | 154.2 | 242 | 2,257 | 8.0 |

°data not included in determining mean, median

TABLE 3

Titers of Rabbit Antisera to M-Protein Following Immunization with Various Type A Influenza Viruses

| | M-Protein | | | Peptide #2 | | |
|---|---|---|---|---|---|---|
| | Serum Titers | | Ratio Immune/ | Serum Titers | | Ratio Immune/ |
| Virus | Preimmune | Immune | Preimmune | Preimmune | Immune | Preimmune |
| H1N1[a] | | | | | | |
| A/NWS/33[b] | 178 | 161,889 | 909.5 | 188 | 6,387 | 34.0 |
| A/NWS/33[c] | 104 | 336,634 | 3236.9 | 110 | 6,384 | 58.0 |
| A/PR/8/34 | 810 | 313,096 | 386.5 | 240 | 18,086 | 75.4 |
| A/Swine/Cam/39 | 479 | 168,042 | 350.8 | 657 | 2,177 | 3.3 |
| A/USSR/90/77 | 741 | 158,161 | 213.4 | 2382 | 2,855 | 1.2 |
| A/Brazil/11/78 | 730 | 47,809 | 65.5 | 1746 | 5,223 | 3.0 |
| H1N2 | | | | | | |
| X-7[e] | 143 | 50,957 | 356.3 | 671 | 1,951 | 2.9 |
| X-7(F1)[f] | 226 | 68,592 | 303.5 | 1084 | 2,377 | 2.2 |
| PR8/HK[g] #2071 | 188 | 15,405 | 81.9 | 237 | 805 | 3.4 |
| PR8/HK[h] #2072 | 155 | 24,300 | 156.8 | 270 | 3,344 | 12.4 |
| PR8/HK[i] #3642 | 232 | 70,956 | 305.8 | 182 | 7,002 | 38.5 |
| PR8/HK[j] #3643 | 153 | 23,183 | 151.5 | 102 | 7,229 | 70.9 |
| PR8/HK[k] #3644 | 73 | 35,700 | 489.0 | 30 | 6,766 | 225.5 |
| H2N2 | | | | | | |
| A/RI/5$^{-}$/57 | 142 | 20,889 | 147.1 | 217 | 774 | 3.6 |
| H3N2 | | | | | | |
| A/Victoria/3/75 | 749 | 35,182 | 47.0 | 759 | 6,321 | 8.3 |

TABLE 3-continued Titers of Rabbit Antisera to M-Protein Following Immunization with Various Type A Influenza Viruses

| Virus | M-Protein | | | Peptide #2 | | |
|---|---|---|---|---|---|---|
| | Serum Titers | | Ratio Immune/ | Serum Titers | | Ratio Immune/ |
| | Preimmune | Immune | Preimmune | Preimmune | Immune | Preimmune |
| A/Texas/1/77 | 1010 | 2,046 | 2.0 | 1298 | 685 | 0.5 |
| X-31[l] | 699 | 49,851 | 71.3 | 357 | 1,707 | 4.8 |
| X-73[m] | 590 | 49,239 | 83.5 | 4880 | 2,116 | 0.4 |
| X-79[n] | 2403 | 43,011 | 17.9 | 894 | 1,089 | 1.2 |
| H7N2 | | | | | | |
| X-74[o] | 207 | 18,528 | 89.5 | 53 | 684 | 12.9 |
| Mean | 501 | 84,674 | 373.3 | 818 | 4,198 | 28.1 |
| Median | 229 | 48,524 | 154.2 | 314 | 2,616 | 4.2 |

*data not included in determining mean, median

TABLE 4

Titers of Rabbit Antisera to M-Protein Following Immunization with Various Type A Influenza Viruses

| Virus | M-Protein | | | Peptide #3 | | |
|---|---|---|---|---|---|---|
| | Serum Titers | | Ratio Immune/ | Serum Titers | | Ratio Immune/ |
| | Preimmune | Immune | Preimmune | Preimmune | Immune | Preimmune |
| H1N1[a] | | | | | | |
| A/NWS/33[b] | 178 | 161,889 | 909.5 | 605 | 7,205 | 11.9 |
| A/NWS/33[c] | 104 | 336,634 | 3236.9 | 254 | 15,354 | 60.4 |
| A/PR/8/34 | 810 | 313,096 | 386.5 | 4583 | 19,583 | 4.3 |
| A/Swine/Cam/39 | 479 | 168,042 | 350.8 | N.D. | 2,066* | — |
| A/USSR/90/77 | 741 | 158,161 | 213.4 | 1954 | 5,449 | 2.8 |
| A/Brazil/11/78 | 730 | 47,809 | 65.5 | 741 | 1,516 | 2.0 |
| H1N2 | | | | | | |
| X-7[e] | 143 | 50,957 | 356.3 | 257 | 254 | 1.0 |
| X-7(F1)[f] | 226 | 68,592 | 303.5 | 2197 | 2,004 | 0.9 |
| PR8/HK[g] #2071 | 188 | 15,405 | 81.9 | 1938 | 509 | 0.3 |
| PR8/HK[h] #2072 | 155 | 24,300 | 156.8 | 108 | 7,973 | 73.8 |
| PR8/HK[i] #3642 | 232 | 70,956 | 305.8 | 523 | 5,537 | 10.6 |
| PR8/HK[j] #3643 | 153 | 23,183 | 151.5 | N.D. | 1,210* | — |
| PR8/HK[k] #3644 | 73 | 35,700 | 489.0 | 176 | 2,239 | 12.7 |
| H2N2 | | | | | | |
| A/RI/5−/57 | 142 | 20,889 | 147.1 | 609 | 2,321 | 3.8 |
| H3N2 | | | | | | |
| A/Victoria/3/75 | 749 | 35,182 | 47.0 | 584 | 6,702 | 11.5 |
| A/Texas/1/77 | 1010 | 2,046 | 2.0 | 639 | 176 | 0.3 |
| X-31[l] | 699 | 49,851 | 71.3 | N.D. | 885* | — |
| X-73[m] | 590 | 49,239 | 83.5 | 471 | 5,974 | 12.7 |
| X-79[n] | 2403 | 43,011 | 17.9 | 5750 | 3,031 | 0.5 |
| H7N2 | | | | | | |
| X-74[o] | 207 | 18,528 | 89.5 | 136 | 1,361 | 10.0 |
| Mean | 501 | 84,674 | 373.3 | 1266 | 5,129 | 12.9 |
| Median | 229 | 48,524 | 154.2 | 605 | 3,031 | 4.3 |

*data not included in determining mean, median
Key to Superscripts: Tables 2, 3 and 4
[a]Subtype with reference to surface antigens, H(HA, hemaglutinin), and N(NA, neuraminidase).
[b]Virus passed in monkey kidney cells (serum preparation #2042).
[c]Virus passed in monkey kidney cells (serum preparation #2043).
[d]Recombinant virus containing A/Swine/NJ/11/76 surface antigens and A/PR8/34 internal antigens.
[e]Recombinant virus containing HA from A/NWS/33 and NA from A/RI/5+/57.
[f]Recombinant virus containing HA from A/NWS/33 and NA from A/RI/5+/57.
[g]Recombinant virus containing HA from A/PR8/34, Cambridge line, and NA from A/Hong Kong/8/68, X623 II 3a, J. L. Schulman (serum preparation #2071).
[h]See g, serum preparation #2072.
[i]See g, serum preparation #3642.
[j]See g, serum preparation #3643.
[k]See g, serum preparation #3644.
[l]High-yielding recombinant virus strain containing HA and NA from A/Aichi/68 and internal antigens including M-protein from A/PR8/34.
[m]High-yielding recombinant virus strain containing HA and NA from A/Bangkok/79.
[n]High-yielding recombinant virus strain containing HA and NA from A/Philippines/82.
[o]Recombinant virus containing HA from Heql/Prague/56 and NA from A/Bangkok/79.

What is claimed is:

1. A synthetic polypeptide exhibiting influenza virus antigenic reactivity and selected from the group consisting of polypeptides of from about 15 to about 25 amino acids in length and substantially corresponding to a 15 to 25 amino acid sequence of the 79–104 region of the type A influenza virus matrix protein; polypeptides of from about 9 to about 15 amino acids in length and substantially corresponding to a 9 to 15 amino acid sequence of the 64–80 region of the type A influenza virus matrix protein; and polypeptides of from about 12 to about 21 amino acids in length and substantially corresponding to a 12 to 21 amino acid sequence of the 149–169 region of the type A influenza virus matrix protein.

2. The synthetic polypeptide of claim 1 being from 15 to 20 amino acids in length and substantially corresponding to the 80–103 region of the type A influenza virus matrix protein.

3. The synthetic polypeptide of claim 2 being 18 amino acids in length and having the amino acid sequence H-Ala-Leu-Asn-Gly-Asn-Gly-Asp-Pro-Asn-Asn-Met-Asp-Lys-Ala-Val-Lys-Leu-Tyr-OH.

4. The synthetic polypeptide of claim 1 being from 13 to 15 amino acids in length and substantially corresponding to the 66–80 region of the type A influenza virus matrix protein.

5. The synthetic polypeptide of claim 4 being 13 amino acids in length and having the amino acid sequence H-Leu-Thr-Val-Pro-Ser-Glu-Arg-Gly-Leu-Gln-Arg-Arg-Arg-OH.

6. The synthetic polypeptide of claim 1 being from 13 to 19 amino acids in length and substantially corresponding to the 150–168 region of the type A influenza virus matrix protein.

7. The synthetic peptide of claim 6 being 15 amino acids in length and having the amino acid sequence H-Glu-Gln-Ile-Ala-Asp-Ser-Gln-His-Arg-Ser-His-Arg-Gln-Met-Val-OH.

8. A synthetic polypeptide of claim 1 in salt form.

9. A polypeptide of claim 1 further comprising a radiolabel.

10. A polypeptide of claim 1 wherein the carboxyl-terminal amino acid has been converted to an amide group.

11. A polypeptide of claim 1 wherein the amino-terminal amino acid has been blocked with an acyl group.

12. A conjugate comprising a macromolecular carrier having attached thereto a synthetic polypeptide of claim 1.

13. The conjugate of claim 12 wherein the carrier is a protein.

14. The conjugate of claim 12 wherein the carrier comprises a label.

15. The conjugate of claim 14 wherein the label is a radiolabel.

16. The conjugate of claim 14 wherein the label is a fluorolabel.

17. The conjugate of claim 14 wherein the label is an enzyme label.

18. An antibody specific to a polypeptide of claim 1.

19. An antibody specific to a conjugate of claim 12.

20. A method for determining the presence of influenza virus in a sample which method comprises contacting the sample with an antibody of claim 18 under immunologic reaction conditions and detecting the immunologic binding between the virus and the antibody.

21. A method for determining the presence of influenza virus in a sample which method comprises contacting the sample with an antibody of claim 19 under immunologic reaction conditions and detecting the immunologic binding between the virus and the antibody.

22. A method for determining the presence of antibody to influenza virus in a sample which method comprises contacting the sample with a polypeptide of claim 1 under immunologic reaction conditions and detecting the immunologic binding between the peptide and the antibody.

23. A method for determining the presence of antibody to influenza virus in a sample which method comprises contacting the sample with a conjugate of claim 9 under immunologic reaction conditions and detecting the immunologic binding between the peptide and the antibody.

* * * * *